(12) United States Patent
Mizutani et al.

(10) Patent No.: US 10,091,426 B2
(45) Date of Patent: *Oct. 2, 2018

(54) INFORMATION PROCESSING APPARATUS, INFORMATION PROCESSING METHOD, AND PROGRAM

(71) Applicant: Sony Corporation, Tokyo (JP)

(72) Inventors: Yoichi Mizutani, Saitama (JP); Shigeatsu Yoshioka, Kanagawa (JP); Yoshihiro Wakita, Tokyo (JP); Masashi Kimoto, Tokyo (JP); Naoki Tagami, Tokyo (JP)

(73) Assignee: Sony Corporation, Tokyo (JP)

( * ) Notice: Subject to any disclaimer, the term of this patent is extended or adjusted under 35 U.S.C. 154(b) by 77 days.

This patent is subject to a terminal disclaimer.

(21) Appl. No.: 14/875,196

(22) Filed: Oct. 5, 2015

(65) Prior Publication Data

US 2016/0027170 A1 Jan. 28, 2016

Related U.S. Application Data

(60) Continuation of application No. 14/276,109, filed on May 13, 2014, now Pat. No. 9,177,375, which is a (Continued)

(30) Foreign Application Priority Data

Nov. 27, 2009 (JP) .................................. 2009-269495

(51) Int. Cl.
*G06K 9/00* (2006.01)
*H04N 5/232* (2006.01)
(Continued)

(52) U.S. Cl.
CPC .......... *H04N 5/23293* (2013.01); *G06F 3/14* (2013.01); *G06F 19/321* (2013.01);
(Continued)

(58) Field of Classification Search
CPC ....... G06T 7/0012; G06T 11/00; G06T 11/60; G02B 6/4221; G02B 21/34; G06F 3/14; H04N 5/23293
See application file for complete search history.

(56) References Cited

U.S. PATENT DOCUMENTS 6,466,690 B2 * 10/2002 Bacus ..................... G06F 19/20
382/128
7,732,792 B2 * 6/2010 Matsuoka ........... G03F 7/70616
250/306

(Continued)

FOREIGN PATENT DOCUMENTS

| CN | 101317749 | 12/2008 |
| CN | 101505650 | 8/2009 |

(Continued)

OTHER PUBLICATIONS

The State Intellectual Property Office of P.R. C., Notification of the First Office Action, issued in connection with Chinese Application Serial No. 201010553713.2, dated Nov. 28, 2012. (36 pages).

(Continued)

*Primary Examiner* — Shefali Goradia
(74) *Attorney, Agent, or Firm* — K&L Gates LLP

(57) ABSTRACT

In one example embodiment, an information processing apparatus, for an observed image associated with an observation target object (e.g., a section of biological tissue), associates and stores position information and observation magnification information. In this embodiment, the information processing apparatus causes a display device to: (i) display an image associated with the observation target object; (ii) indicate the first positional information of the first observed image; and (iii) indicate the first observation magnification information of the first observed image.

48 Claims, 12 Drawing Sheets

Related U.S. Application Data division of application No. 12/900,000, filed on Oct. 7, 2010, now Pat. No. 8,761,468.

(51) Int. Cl.
- *G06F 19/00* (2018.01)
- *G06T 11/00* (2006.01)
- *G06T 7/00* (2017.01)
- *G06T 11/60* (2006.01)
- *G06F 3/14* (2006.01)

(52) U.S. Cl.
CPC ............ *G06T 7/0012* (2013.01); *G06T 11/00* (2013.01); *G06T 11/60* (2013.01)

(56) References Cited

U.S. PATENT DOCUMENTS

| | | | |
|---|---|---|---|
| 7,876,948 B2* | 1/2011 | Wetzel | G01B 7/003 348/79 |
| 8,410,993 B2* | 4/2013 | Jenks | G06F 3/1446 345/1.3 |
| 8,515,141 B2 | 8/2013 | Sawa et al. | |
| 9,013,572 B2* | 4/2015 | Fujisawa | H01J 37/222 250/307 |
| 2002/0025082 A1* | 2/2002 | Kaushikkar | B82Y 15/00 382/294 |
| 2003/0039384 A1* | 2/2003 | Bacus | G06F 19/20 382/128 |
| 2003/0123717 A1 | 7/2003 | Bacus et al. | |
| 2005/0281476 A1* | 12/2005 | Tanikawa | A61B 5/0059 382/255 |
| 2006/0064321 A1 | 3/2006 | Sasano et al. | |
| 2008/0303898 A1 | 12/2008 | Nishimura | |
| 2011/0181688 A1 | 7/2011 | Miyamoto et al. | |
| 2011/0205353 A1* | 8/2011 | Fujisawa | H01J 37/222 348/80 |
| 2013/0187954 A1 | 7/2013 | Saito et al. | |

FOREIGN PATENT DOCUMENTS

| | | |
|---|---|---|
| JP | 06-275226 | 9/1994 |
| JP | 2004-348095 | 12/2004 |
| JP | 2005-266718 | 9/2005 |
| JP | 2005-283376 | 10/2005 |
| JP | 2006-223850 | 8/2006 |
| JP | 2009-037250 | 2/2009 |

OTHER PUBLICATIONS

The State Intellectual Property Office of P.R. C., Notification of the Second Office Action, issued in connection with Chinese Application Serial No. 201010553713.2, dated Jul. 19, 2013. (60 pages).

Japanese Patent Office, Notice of refusal issued in connection with Japanese Patent Application No. 2009-269495, dated Sep. 3, 2013. (4 pages).

Extended European Search Report issued in connection with European Patent Application 10014796.6, dated Sep. 10, 2015. (6 pages).

Communication pursuant to Article 94(3) EPC for App. No. 10 014 796.6-1126 dated Feb. 19, 2018 (5 pages).

\* cited by examiner

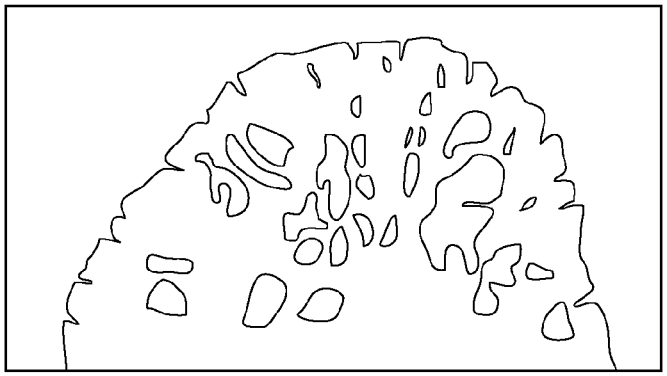
Partial image at 1.25x (Display range D1)
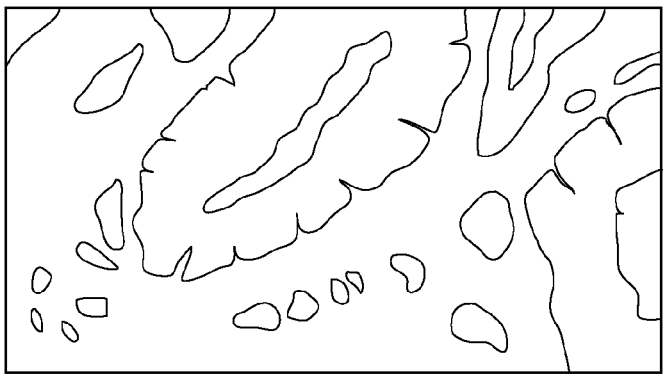
Partial image at 20x (Display range D3)
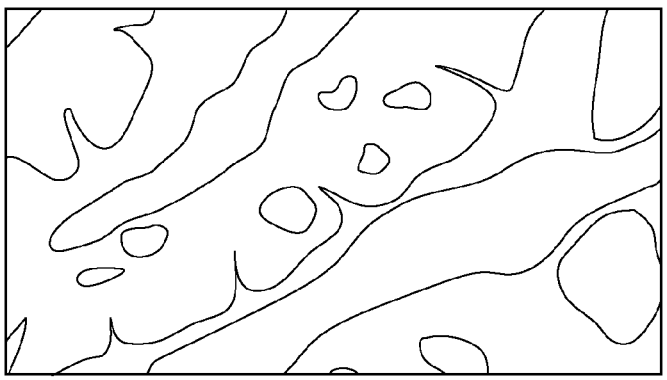
Partial image at 40x (Display range D5)

20

| Sampling | Resolution | Magnification | Positional information (coordinates) | Time period | .... |
|---|---|---|---|---|---|
| 1 | a × b | 1.25 | (x1,y1) | 00h00m00s | .... |
| 2 | a × b | 1.25 | (x2,y2) | 00h00m02s | .... |
| ⋮ | ⋮ | ⋮ | ⋮ | ⋮ | ⋮ |
| N1 | g × h | 20 | (xN1,yN1) | 00h00m10s | .... |
| ⋮ | ⋮ | ⋮ | ⋮ | ⋮ | ⋮ |
| N2 | k × l | 40 | (xN2,yN2) | 00h00m56s | .... |
| ⋮ | ⋮ | ⋮ | ⋮ | ⋮ | ⋮ |

FIG.7

INFORMATION PROCESSING APPARATUS, INFORMATION PROCESSING METHOD, AND PROGRAM

CROSS REFERENCES TO RELATED APPLICATIONS

The present application is a continuation of U.S. application Ser. No. 14/276,109, filed on May 13, 2014, which is a divisional of U.S. application Ser. No. 12/900,000, filed Oct. 7, 2010 and has issued as U.S. Pat. No. 8,761,468 on Jun. 24, 2014, which claims priority to Japanese Patent Application No. JP 2009-269495, filed in the Japanese Patent Office on Nov. 27, 2009, the entire content of which is being incorporated herein by reference.

BACKGROUND

In a field of medicine, pathology, or the like, there has been proposed a system that digitizes an image of a cell, a tissue, an organ, or the like of a living body, that is obtained by an optical microscope, to examine the tissue or the like by a doctor or a pathologist or diagnose a patient based on the digitized image.

For example, Japanese Patent Application Laid-open No. 2009-37250 (hereinafter, referred to as Patent Document 1) discloses a method in which an image optically obtained by a microscope is digitized by a video camera with a CCD (charge coupled device), a digital signal is input to a control computer system, and the image is visualized on a monitor. A pathologist performs examination while watching the image displayed on the monitor (see, for example, paragraphs 0027 and 0028 and FIG. 5 of Patent Document 1).

Generally, as a magnification of a microscope is increased, an observation area thereof becomes smaller relative to an entire observation target. For example, a pathologist often scans and observes the entire observation target by a microscope and observes a part of the entire observation target at a particularly high magnification to examine the target. In such an examination, if there is a disorder in an area where the pathologist does not observe in the observation target, that is, a pathologist misses a disorder, a significant problem may arise later.

In view of the above-mentioned circumstances, it is desirable to provide an information processing apparatus, an information processing method, and a program for avoiding a risk of missing in the observation target with a microscope by a user.

It is also desirable to provide an information processing apparatus, an information processing method, and a program that are useful for education in fields in which such an observation target is treated.

SUMMARY

The present disclosure relates to an information processing apparatus, an information processing method, and a program for controlling display of an image obtained by a microscope in a field of medicine, pathology, biology, materials science, or the like.

In an example embodiment, the information processing apparatus includes a processor and a memory device operatively coupled to the processor, the memory device storing instructions that cause the processor, in cooperation with the memory device, to: (a) for a first observed image associated with an observation target object (e.g., a section of biological tissue), associate and store first position information and first observation magnification information; and (b) cause a display device to: (i) display an image associated with the observation target object; (ii) indicate the first positional information of the first observed image; and (iii) indicate the first observation magnification information of the first observed image. In an example embodiment, the first observed image is observed by a microscope.

In an example embodiment, the displayed image associated with the observation target object includes an entire image of the observation target object. In this example, the instructions cause the display device to display the first observed image such that the first observed image is included in the displayed entire image of the observation target object.

In an example embodiment, the first observed image is from a plurality of different images associated with the observation target object. In an example embodiment, the plurality of different images form an image pyramid structure.

In an example embodiment, the displayed image has one of a first resolution and a second resolution.

In an example embodiment, each of the indicated first positional information and the indicated first observation magnification information overlap the displayed image.

In an example embodiment, the instructions cause the display device to indicate the first positional information by indicating positional information of the entire first observed image, wherein the indication of the entire first observed image overlaps the displayed image.

In an example embodiment, the instructions, cause the processor to, in response to a request for a change in observance from the first observed image to a second image to be observed, associate and store the first position information and the first observation magnification information.

In an example embodiment, the instructions cause the processor to cause the display device to indicate the first positional information using an image (e.g., an arrow image).

In an example embodiment, the image used to indicate the first positional information has a color based on the first observation magnification information.

In an example embodiment, the image used to indicate the first positional information has a size based on the first observation magnification information.

In an example embodiment, the instructions cause the processor to cause the display device to indicate the first positional information and the first observation magnification information using outline images which indicate an entire outline wherein a combination of individually observed images are combined.

In an example embodiment, the instructions cause the processor to cause the display device to indicate an amount of time the first observed image was observed.

In an example embodiment, the instructions cause the processor to cause the display device to indicate user identification information associated with the first observed image.

In an example embodiment, the instructions cause the processor to: (a) for a second observed image associated with the observation target object, associate and store second position information and second observation magnification information; (b) indicate the second positional information of the second observed image; and (c) indicate the second observation magnification information of the second observed image.

In an example embodiment, the instructions cause the processor to cause the display device to: (a) indicate the first positional information using a first image; and (b) indicate the second positional information using a second image such that a temporal order of the first observed image and the second observed image is indicated.

In an example embodiment, the instructions cause the processor to associate and store first position information and first observation magnification information based on a predetermined sampling period.

In an example embodiment, the method of operating the information processing apparatus includes: (a) causing a processor to execute the instructions to, for a first observed image associated with an observation target object, associate and store first position information and first observation magnification information; and (b) causing the processor to execute the instructions to cause a display device to: (i) display an image associated with the observation target object; (ii) indicate the first positional information of the first observed image; and (iii) indicate the first observation magnification information of the first observed image.

In an example embodiment, the computer-readable medium storing instructions causes an information processing apparatus to: (a) for a first observed image associated with an observation target object, associate and store first position information and first observation magnification information; and (b) cause a display device to: (i) display an image associated with the observation target object; (ii) indicate the first positional information of the first observed image; and (iii) indicate the first observation magnification information of the first observed image.

In an example embodiment, the information processing apparatus includes a processor and a memory device operatively coupled to the processor, the memory device storing instructions that cause the processor, in cooperation with the memory device, to, for a first observed image associated with an observation target object (e.g., a section of biological tissue), associate and store first position information and first observation magnification information.

In an example embodiment, the instructions cause the processor to, in response to a request for a change in observance from the first observed image to a second image to be observed, associate and store the first position information and the first observation magnification information.

In an example embodiment, the instructions, when executed by the processor, cause the processor to associate and store first position information and first observation magnification information based on a predetermined sampling period.

In an example embodiment, the method of operating an information processing apparatus includes causing a processor to execute the instructions to, for a first observed image associated with an observation target object, associate and store first position information and first observation magnification information.

In an example embodiment, the computer-readable medium stores instructions structured to cause an information processing apparatus to, for a first observed image associated with an observation target object, associate and store first position information and first observation magnification information.

In an example embodiment, the information processing apparatus includes a processor and a memory device operatively coupled to the processor, the memory device storing instructions that cause the processor, in cooperation with the memory device, to cause a display device to: (a) display a first image associated with an observation target object (e.g., a section of biological tissue); (b) indicate first positional information of a first observed image; and (c) indicate first observation magnification information of the first observed image.

In an example embodiment, each of the indicated first positional information and the indicated first observation magnification information overlap said displayed first image.

In an example embodiment, the instructions cause the processor to cause the display device to indicate the first positional information by indicating positional information of the entire first observed image, said indication of the entire first observed image overlapping said displayed first image.

In an example embodiment, the instructions cause the processor to, in response to a request for a change in observance from the first observed image to a second image to be observed, associate and store the first position information and the first observation magnification information.

In an example embodiment, the instructions cause the processor to cause the display device to indicate the first positional information using a second image (e.g., an arrow image). In an example embodiment, the second image used to indicate the first positional information has a color based on the first observation magnification information. In an example embodiment, the second image used to indicate the first positional information has a size based on the first observation magnification information.

In an example embodiment, the instructions cause the processor to cause the display device to indicate the first positional information and the first observation magnification information using outline images which indicate an entire outline wherein a combination of individually observed images are combined.

In an example embodiment, the instructions cause the processor to cause the display device to indicate an amount of time the first observed image was observed.

In an example embodiment, the instructions cause the processor to cause the display device to indicate user identification information associated with the first observed image.

In an example embodiment, the instructions, when executed by the processor, cause the processor to: (a) indicate second positional information of a second observed image; and (b) indicate second observation magnification information of a second observed image.

In an example embodiment, the instructions cause the processor to cause the display device to: (a) indicate the first positional information using a second image; and (b) indicate the second positional information using a third image such that a temporal order of the first observed image and the second observed image is indicated.

In an example embodiment, the instructions cause the processor to associate and store first position information and first observation magnification information based on a predetermined sampling period.

In an example embodiment, the method of operating an information processing apparatus includes: (a) causing a processor to execute the instructions to cause a display device to display a first image associated with an observation target object; (b) causing the processor to execute the instructions to cause the display device to indicate first positional information of a first observed image; and (c) causing the processor to execute the instructions to cause the display device to indicate first observation magnification information of the first observed image.

In an example embodiment, the computer-readable medium stores instructions structured to cause an information processing apparatus to: (a) display a first image associated with an observation target object; (b) indicate first positional information of a first observed image; and (c) indicate first observation magnification information of the first observed image.

In an example embodiment, the information processing apparatus includes a processor and a memory device operatively coupled to the processor, the memory device storing instructions that cause the processor, in cooperation with the memory device, to: (a) for a first image associated with a section of biological tissue which is observed by a microscope, associate and store first position information; and (b) cause a display device to: (i) display an image associated with the section of biological tissue; and (ii) indicate the first positional information of the first observed image.

As described above, it is possible to avoid the risk of missing the observation target using the microscope by the user.

These and other objects, features and advantages of the present disclosure will become more apparent in light of the following detailed description of best mode embodiments thereof, as illustrated in the accompanying drawings.

Additional features and advantages are described herein, and will be apparent from the following Detailed Description and the figures.

BRIEF DESCRIPTION OF THE FIGURES

FIGS. 6A, 6B, and 6C are diagrams each showing an example of a partial image;

FIG. 7 is a lookup table of history information of the partial image stored in a storage unit in FIG. 4;

DETAILED DESCRIPTION

Hereinafter, embodiments of the present disclosure will be described with reference to the drawings.

First Embodiment (Structure of Information Processing Apparatus)

Figure 1:
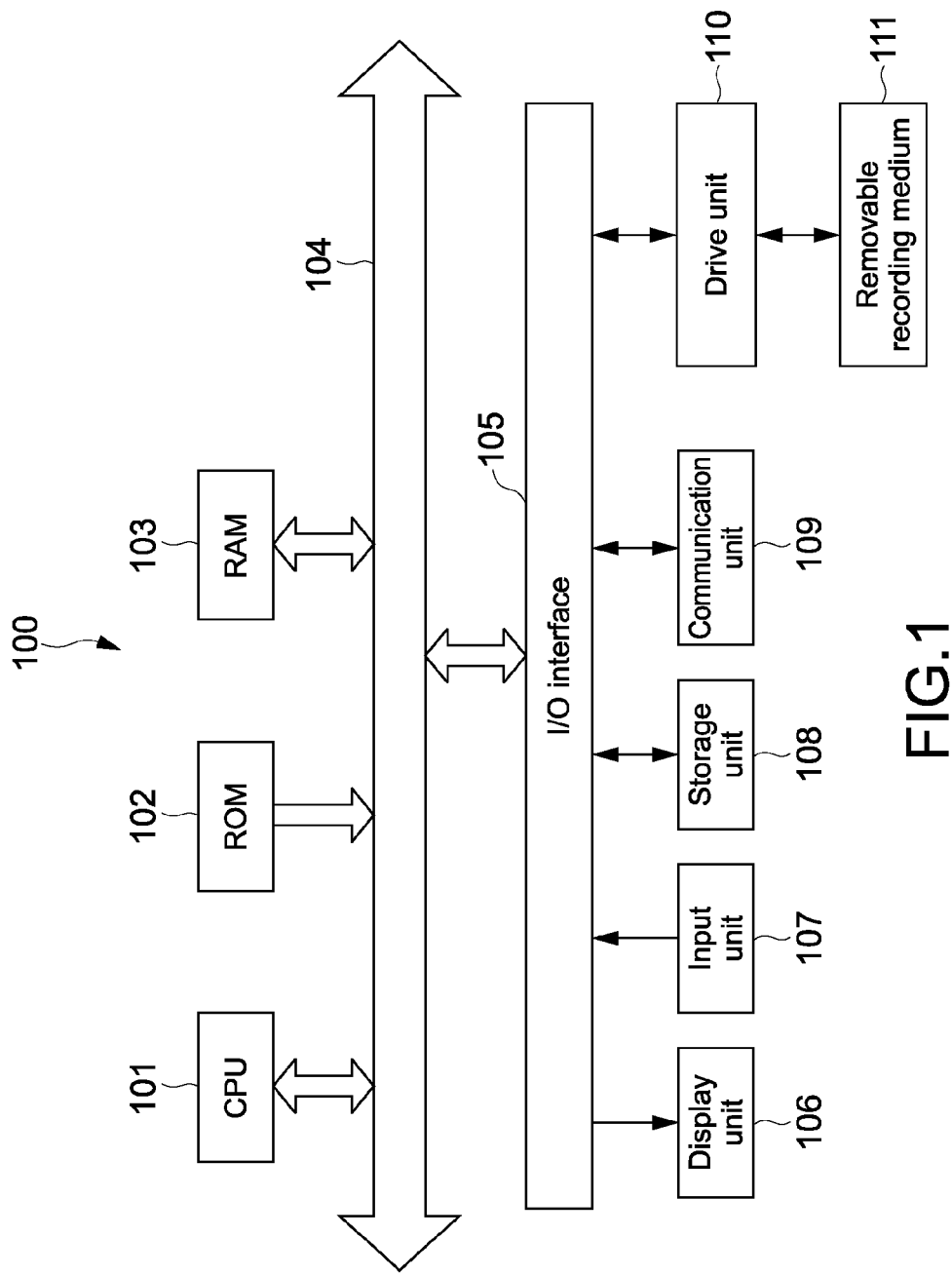
FIG. 1 is a block diagram showing the structure of an information processing system including at least an information processing apparatus according to a first embodiment of the present disclosure.

FIG. 1 is a block diagram showing the structure of an information processing system including at least an information processing apparatus according to an embodiment of the present disclosure. As the information processing apparatus, a PC (personal computer) 100 is used, for example.

The PC 100 includes a CPU (central processing unit) 101, a ROM (read only memory) 102, a RAM (random access memory) 103, an input and output interface (hereinafter, abbreviated as I/O interface) 105, and a bus 104 that connects those components with one another.

To the I/O interface 105, a display unit 106, an input unit 107, a storage unit 108, a communication unit 109, a drive unit 110, and the like are connected.

The display unit 106 is a display device that uses liquid crystal, EL (electro-luminescence), a CRT (cathode ray tube), or the like.

The input unit 107 is, for example, a pointing device, a keyboard, a touch panel, or another operation apparatus. In the case where the input unit 107 includes a touch panel, the touch panel may be integrated with the display unit 106.\

The storage unit 108 is a non-volatile storage device such as an HDD (hard disk drive), a flash memory, and another solid-state memory.

The drive unit 110 is a device capable of driving a removable recording medium 111 such as an optical recording medium, a floppy (registered trademark) disk, a magnetic recording tape, and a flash memory. In contrast, the storage unit 108 is often used as a device that is previously included in the PC 100 and mainly drives a recording medium that is not removable.

The communication unit 109 is a modem, a router, or another communication apparatus that is connectable to a LAN (local area network), a WAN (wide area network), or the like and is used for communicating with another device. The communication unit 109 may perform either one of a wired communication or a wireless communication. The communication unit 109 is used separately from the PC 100 in many cases.

Figure 2:
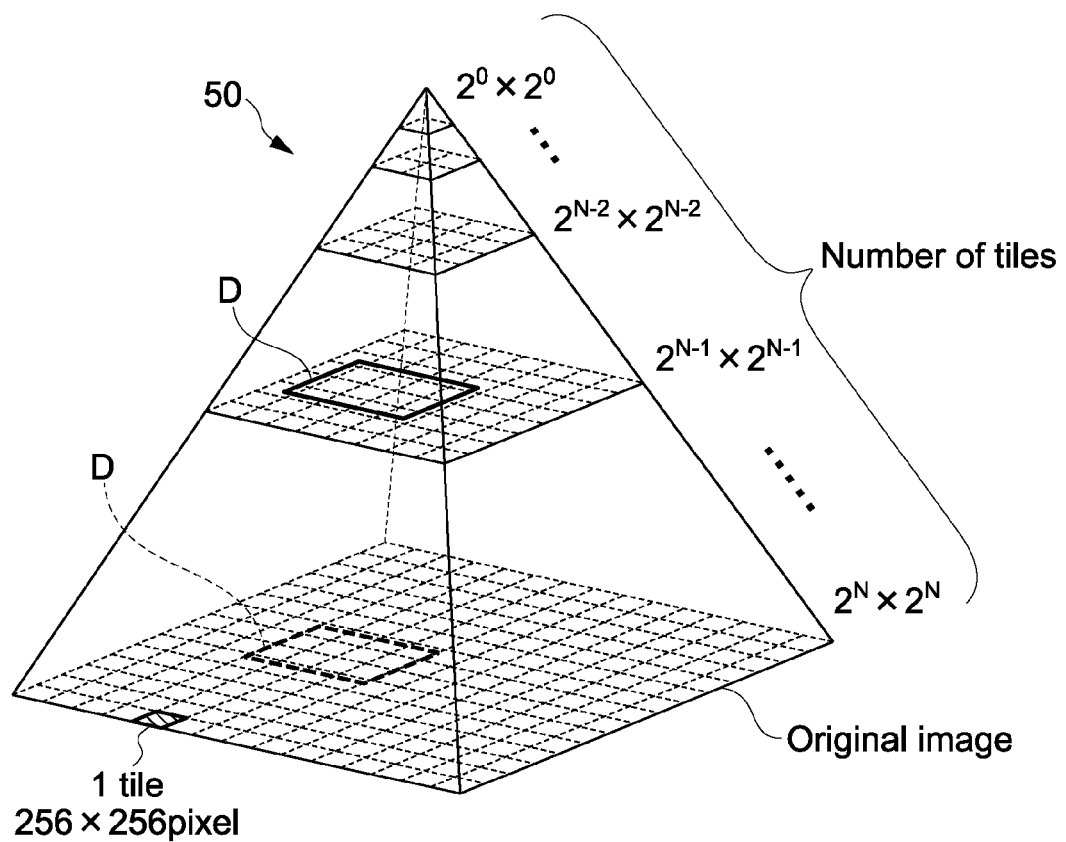
FIG. 2 is a diagram showing an image pyramid structure for explaining a display principle thereof.

Next, a description will be given on an image that is obtained by an optical microscope (not shown) and is mainly stored in the storage unit 108 of the PC 100 and on a principle of displaying the image. FIG. 2 is a diagram showing an image pyramid structure for explaining the display principle.

An image pyramid structure 50 in this embodiment is an image group (entire image group) generated at a plurality of resolutions with respect to one image obtained from one observation target object 15 (see, FIG. 3) by the optical microscope. On a lowermost part of the image pyramid structure 50, a largest image is disposed, and on an uppermost part thereof, a smallest image is disposed. A resolution of the largest image is 50×50 (Kpixel: kilopixel) or 40×60 (Kpixel), for example. A resolution of the smallest image is 256×256 (pixel) or 256×512 (pixel), for example.

That is, when the display unit 106 displays those images at the same magnification (100%) (displays each image by the number of dots that is physically the same as the number of pixels of the images), the largest image is displayed in the largest size, and the smallest image is displayed in the smallest size. Here, a display range of the display unit 106 is represented by D in FIG. 2.

Figure 3:
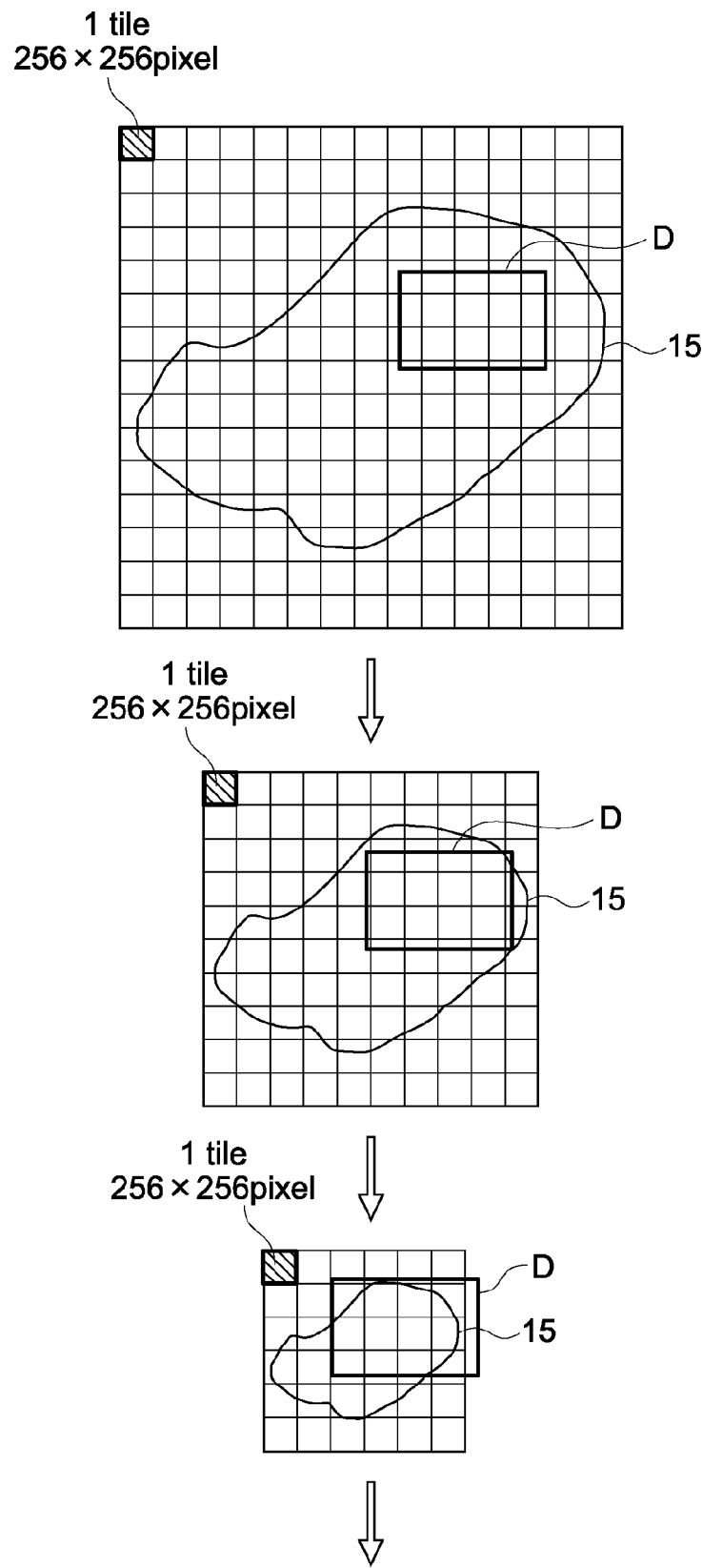
FIG. 3 is a diagram for explaining a procedure at a time when an image group of the image pyramid structure is generated.

FIG. 3 is a diagram for explaining a procedure at a time when the image group of the image pyramid structure 50 is generated.

First, a digital image of an original image obtained at a predetermined observation magnification by an optical microscope (not shown) is prepared. The original image corresponds to the largest image that is the lowermost image of the image pyramid structure 50 shown in FIG. 2, that is, an image at a highest resolution. Therefore, as the lowermost image of the image pyramid structure 50, an image obtained by being observed at a relatively high magnification by the optical microscope is used.

It should be noted that in the field of pathology, generally, a matter obtained by slicing an organ, a tissue, or a cell of a living body, or a part thereof is an observation target object 15. Then, a scanner apparatus (not shown) having a function of the optical microscope reads the observation target object 15 stored on a glass slide, to obtain a digital image and store the digital image obtained into the scanner apparatus or another storage apparatus.

As shown in FIG. 3, the scanner apparatus or a general-purpose computer (not shown) generates, from the largest image obtained as described above, a plurality of images whose resolutions are reduced stepwise, and stores those images in unit of "tile" that is a unit of a predetermined size, for example. The size of one tile is 256×256 (pixel), for example. The image group generated as described above forms the image pyramid structure 50, and the storage unit 108 of the PC 100 stores the image pyramid structure 50. Actually, the PC 100 only has to store the images whose resolutions are different with the images being associated with resolution information items, respectively. It should be noted that the generating and storing the image pyramid structure 50 may be performed by the PC 100 shown in FIG. 1.

The entire image group that forms the image pyramid structure 50 may be generated by a known compression method. For example, a known compression method used at a time when a thumbnail image is generated may be used.

The PC 100 uses software that employs the system of the image pyramid structure 50, to extract a desired image from the image pyramid structure 50 and output the desired image to the display unit 106 in accordance with an input operation through the input unit 107 by the user. Specifically, the PC 100 displays an image of an arbitrary part selected by the user, out of the images at an arbitrary resolution selected by the user. With this operation, the user can get a feeling of observing the observation target object 15 while changing the observation magnification. That is, the PC 100 functions as a virtual microscope. A virtual observation magnification in this case corresponds to a resolution in reality.

Operation of Information Processing Apparatus

Figure 4:
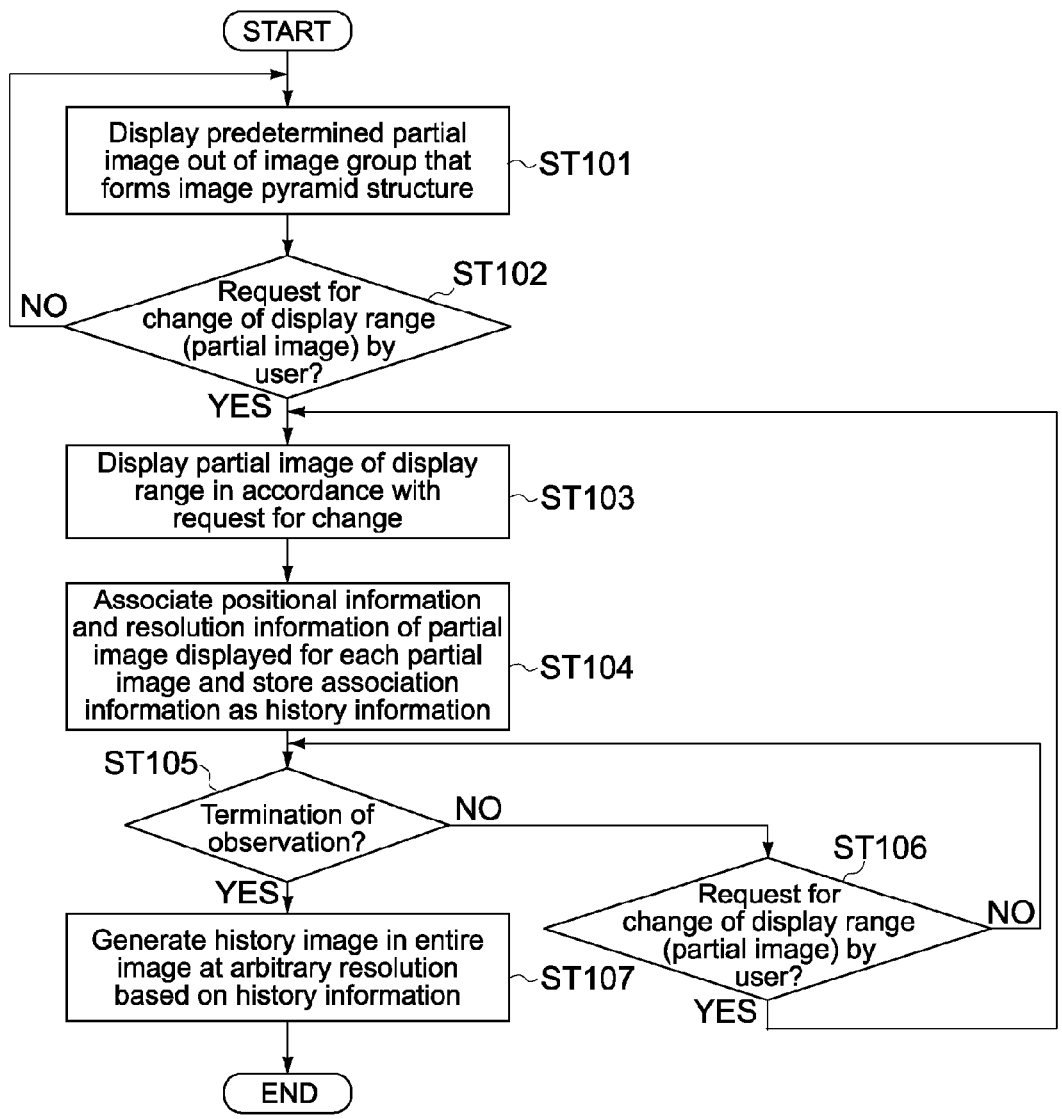
FIG. 4 is a flowchart showing the processing of a PC that is an operation of information processing according to the first embodiment.
Figure 5:
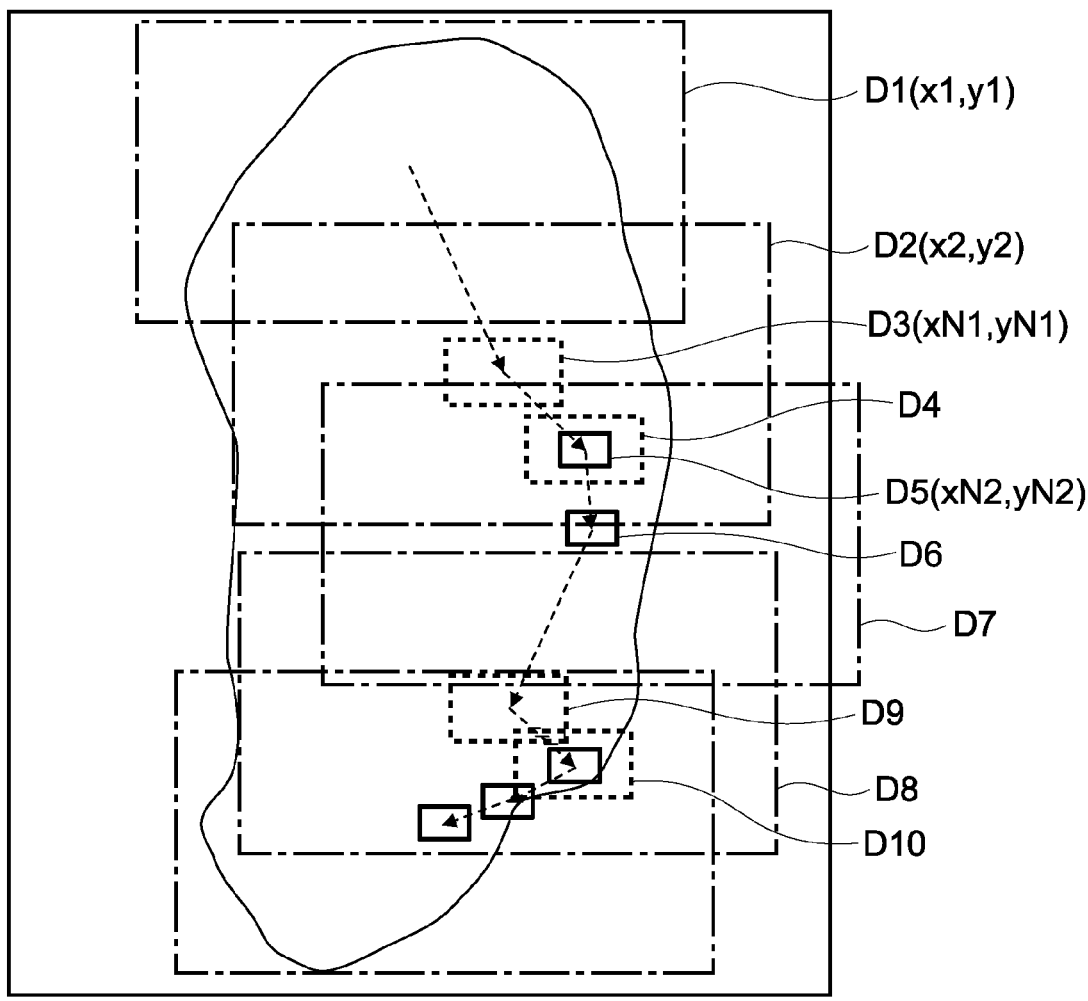
FIG. 5 is a diagram showing an entire image including an image of an observation target object for explaining the operation.

FIG. 4 is a flowchart showing the processing of the PC 100, that is information processing according to this embodiment. FIG. 5 is a diagram showing the entire image including an image of an observation target object for explaining the operation thereof. The entire image is an image at an arbitrary resolution, out of the image group (entire image group) that forms the image pyramid structure 50.

The following processing of the PC 100 is implemented while software stored in the storage unit 108, the ROM 102, or the like and a hardware resource of the PC 100 are cooperated with each other. Specifically, the CPU 101 loads a program that forms the software stored in the storage unit 108, the ROM 102, or the like and executes the program, thereby implementing the following processing.

The user accesses a file including the image group of the image pyramid structure 50 by an input operation using the input unit 107. In accordance with the operation, the CPU 101 of the PC 100 extracts a predetermined partial image from the image pyramid structure 50 stored in the storage unit, and causes the display unit 106 to display the image extracted (Step 101). Out of the image pyramid structure 50, the predetermined partial image accessed by the CPU 100 first may be set as appropriate by default or by the user.

The partial image refers to a part of the image at an arbitrary resolution out of the entire images stored and generated for each resolution as shown in FIGS. 2 and 3. The partial image corresponds to the image in the display range D displayed by the display unit 106. Here, the display range D does not indicate the size of the maximum display range of the display unit 106, but indicates the entire or a part of the display range of the display unit 106. The display range D can be set as appropriate by a user setting, for example. FIGS. 6A to 6C are diagrams each showing the partial image.

In Step 101, the CPU 101 displays a partial image in the entire image having a resolution corresponding to a relatively low resolution (low magnification) in general, for example, an observation magnification of 1.25 times first.

In Step 102, the CPU 101 is in a standby state of an input operation from the input unit 107 by the user.

When the user operates the input unit 107 to change the display range D to a desired range, the CPU 101 causes a partial image corresponding thereto to be displayed (Step 103). As shown in FIG. 5, for example, the user shifts and changes a display range D1 to a display range D2 or scales up the observation magnification from the display range D2, thereby obtaining a display range D3 scaled up (display range is reduced). During this operation, the CPU 101 associates positional information items of partial images that are output with information items on resolutions as observation magnifications for each partial image output. The CPU 101 stores the associated information in the RAM 103 or the storage unit 108 as history information of the partial images (Step 104).

In Steps 101 to 103, the CPU 101, the I/O interface 105, and the like function as output means for outputting the partial image.

A description will be given on an example of a processing in more detail in Steps 103 and 104.

FIG. 7 is a diagram showing a lookup table of the history information of the partial images stored in Step 104.

The assumption is made that the user operates the input unit 107, typically, drags a mouse to shift and change the display range in one entire image from the display range D1 to the display range D2 different therefrom, as shown in FIG. 5. During this operation, the CPU 101 stores, in the RAM 103 or the storage unit 108, the positional information of the partial images corresponding to the display ranges D1 and D2 and positional information of partial images on a way from the display range D1 to the display range D2. In addition, the resolution information of the partial images on the way from the display range D1 to the display range D2 is stored with the resolution information being associated with the partial images. In this example, on the way from the display range D1 to the display range D2, the resolution is not changed, and therefore the same resolution information is stored. In the example shown in FIG. 7, time when sampling is performed is also stored.

The storing processing of history information 20 as described above is performed with a predetermined sampling period. That is, the CPU 101 stores the positional information of all the partial images corresponding to the display range D displayed on the display unit 106 in the one entire image with the predetermined sampling period. The sampling period is 0.1 to 10 seconds, for example, but is not limited to this range.

After the partial image of the display range D2 is output, if the input operation is not performed by the user for a predetermined time period, the CPU 101 may temporarily stop the storing processing of the history information 20.

The positional information of the partial image refers to positional information in the entire image and is managed as coordinate information (x, y), for example. Typically, the coordinate information of a center position of the partial image is managed. However, the coordinate information to be managed is not limited to that of the center position.

The assumption is made that the user shifts the display range from the display range D1 to the display range D2, and then operates the input unit 107 to change the observation magnification from 1.25 times to 20 times. At this time, the CPU 101 changes the display range D from the display range D2 to a display range D3 that is smaller than the display range D2. That is, the CPU 101 displays, out of the entire image at a higher resolution than that of the partial images displayed in the display ranges D1 and D2, a partial image having coordinate information corresponding to the coordinate information of the partial image of the display range D2 as the display range D3.

Depending on the sampling period, during the shift of the observation magnification from 1.25 times to 20 times, the CPU 101 also stores stepwise resolution information and positional information of the partial images during the shift. Alternatively, in the case where the relative position of the partial image in the entire image is not changed, but only the resolution information is changed through the operation by the user, the CPU 101 may omit the storing processing of the stepwise history information (in this case, at least one of the positional information and the resolution information) during the shift or may delete the history information at a predetermined timing thereafter if stored.

Next, the user shifts the display range from the display range D3 to a display range D4, shifts the display range D4 to a display range D5, the magnification of which is higher than that of the display range D4, for example, 40 times, and shifts the display range D5 to a display range D6. During those shifts, the CPU 101 stores the history information 20 of the partial images as shown in FIG. 7. In the example shown in FIG. 7, subsequently, the display range is shifted to the display ranges D7, D8, . . . .

As described above, FIGS. 6A to 6C are diagrams each showing an example of the partial image.

FIG. 6A is a diagram showing the display range D1 shown in FIG. 5 that is a partial image at the observation magnification of 1.25 times.

FIG. 6B is a diagram showing the display range D3 shown in FIG. 5 that is a partial image at the observation magnification of 20 times.

FIG. 6C is a diagram showing the display range D5 shown in FIG. 5 that is a partial image at the observation magnification of 40 times.

In Step 104, the CPU 101, the storage unit 108, and the like function as the storing means for storing the history information 20.

An input operation is performed for closing a file to terminate the observation of the observation target object 15 by the user (YES in Step 105). Then, the CPU 101 generates, based on the history information 20 stored, a history image that represents traces of the partial images and the observation magnifications in the entire image at an arbitrary resolution (Step 107). At this time, at least the CPU 101 functions as an image generation means. Step 107 will be described later.

In the case where the user does not terminate the observation of the observation target object 15, the CPU 101 performs the same processing as Step 102 (Step 106).

The entire image at the arbitrary resolution in which the history image is generated is an arbitrary entire image (including the original image) among the entire image group of the image pyramid structure 50.

Alternatively, the entire image at the arbitrary resolution may be an entire image at an arbitrary resolution formed when necessary for generation of the history image from at least one arbitrary image among the entire image group of the image pyramid structure 50 previously formed. For example, the CPU 101 can generate an entire image at a resolution corresponding to the observation magnification of 30 times, from the entire images of the observation magnifications of 20 times and 40 times which are previously generated and stored by interpolation.

The entire image at the arbitrary resolution generated as described above may be used as a thumbnail image on the PC 100 or another computer. That is, the CPU 101 may store, out of the entire image group of the image pyramid structure 50, at least one entire image among the entire images other than the original image in the storage unit 108 as the thumbnail image. The history image may be generated in the thumbnail image.

Alternatively, the history image may be generated in the entire image on a screen which is to be displayed on the display unit 106 by the PC 100.

As a method of composing the history image into the entire image, a bitmap composition or other known methods can be used.

The timing at which the thumbnail image is generated may be a timing at which the file of the entire image group that forms the image pyramid structure 50 is stored in the storage unit 108 or at which the user accesses the stored file for the first time.

Figure 8:
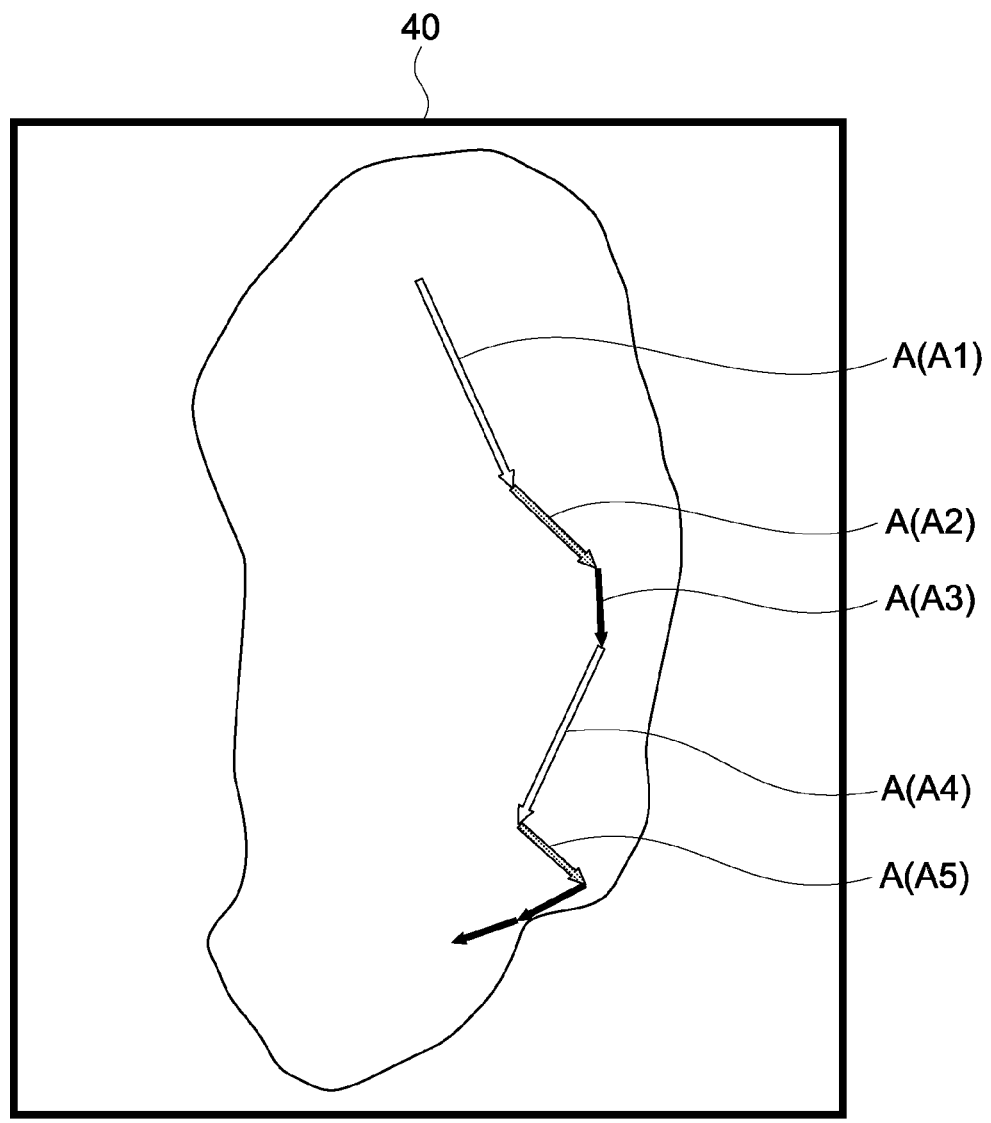
FIG. 8 is a diagram showing an example of an entire image at an arbitrary resolution in which a history image is composed.

FIG. 8 is a diagram showing examples of the entire image (including the original image) at the arbitrary resolution generated as described above, the thumbnail image generated as described above, or the entire image on the screen which is to be displayed on the display unit 106 by the PC 100 (hereinafter, referred to as an entire image at an arbitrary resolution). In Step 107, specifically, the CPU 101 composes, in an entire image 40 at an arbitrary resolution, arrow images A for indicating the positional information of the partial images for each sampling and the traces of the display ranges D corresponding to the resolution information. In FIG. 8, the arrow images A whose colors are different depending on observation magnifications are generated. For example, arrow images A1 and A4 indicate the observation magnification of 1.25 times. Arrow images of A2 and A5 indicate the observation magnification of 20 times. Arrow images of A3 and the like indicate the observation magnification of 40 times.

As described above, in this embodiment, based on the history information 20 as information obtained by associating the positional information and the resolution information of the plurality of partial images, the arrow images A are generated in the entire image 40 at the arbitrary resolution as the history images that indicate the traces and the observation magnifications. As a result, the user can grasp an observation history by referring to the entire image 40 at the arbitrary resolution. Therefore, it is possible to avoid a risk of missing the observation target by the microscope, which is useful particularly for the field of medicine or pathology.

Further, in addition to the grasping of the observation history of him/herself by the user, another user can refer to the observation history. Thus, the observation history is highly useful for checking of the observation history of another person or for education.

In addition, in this embodiment, the colors of the arrow images A are different depending on the observation magnifications. Therefore, it is possible to grasp the observation magnification of the past observation by a person concerned or another person, which increases the convenience.

In this embodiment, the traces of the partial images are indicated by the arrow images A in particular, and therefore the arrow images A function as order emphasizing images. As a result, it is possible to intuitively grasp the temporal order of the past observations by the person concerned or another person.

The order emphasizing images are not limited to the arrow images A, as long as two partial images are connected with a straight-line or curved-line image, for example.

The timing at which the history image is generated by the CPU 101 is not limited to the timing in Step 107 in FIG. 4. For example, the CPU 101 may generate the history image each time at least Step 103 is executed.

In the case where the history information is stored in the RAM 103 in Step 104, when the user closes the file to terminate the observation of the observation target object 15, the CPU 101 stores the history information in the storage unit 108. Of course, even in the case where the history information is stored in the RAM 103, the CPU 101 may periodically store the history information in the storage unit 108.

Second Embodiment

Figure 9:
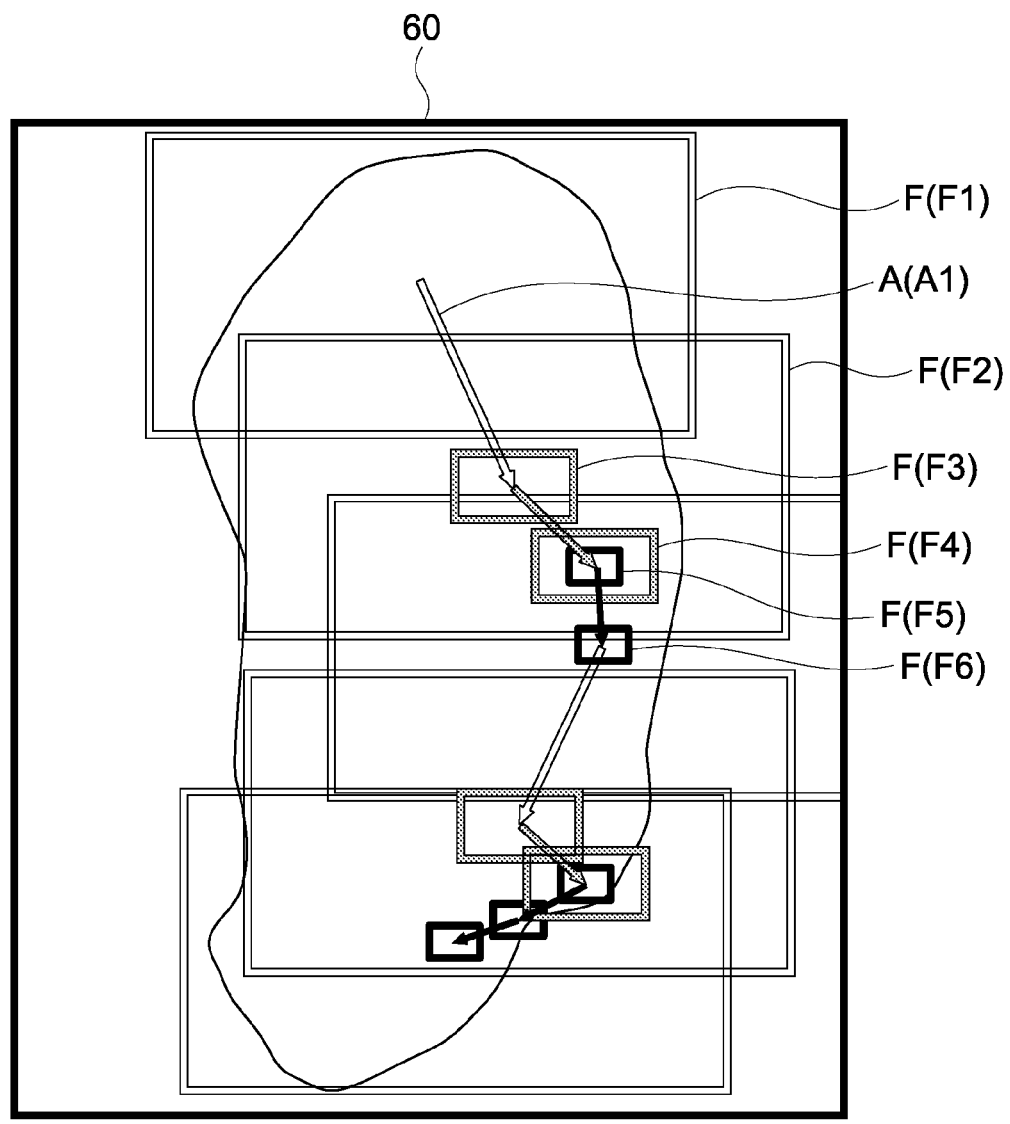
FIG. 9 is a diagram showing an entire image at an arbitrary resolution according to a second embodiment of the present disclosure.

FIG. 9 is a diagram showing an entire image at an arbitrary resolution according to another embodiment of the present disclosure. Entire images at arbitrary resolutions according to the second to fifth embodiments described below are also generated by executing the process shown in FIG. 4 by the CPU 101.

In this embodiment, frame-like images F (F1, F2, F3, . . . ) are composed in an entire image 60 at an arbitrary resolution. The frame-like images F (hereinafter, referred to as frame image F) function as display-range emphasizing images for indicating the display ranges of the respective partial images. Further, frame images F1 and F2 are the display ranges corresponding to the observation magnification of 1.25 times, and frame images F3 and F4 are the display ranges corresponding to the observation magnification of 20 times. Further, frame images F5 and F6 are the display ranges corresponding to the observation magnification of 40 times. The sizes of the frame images F differ depending on the observation magnifications, and therefore the user can intuitively grasp the observation magnification.

In addition, in this embodiment, the frame images F whose colors are different depending on the observation magnifications are generated, thereby making the magnification discrimination easier. As the images that indicate the observation magnifications, images whose frames are indicated with various kinds of lines (that are different in width or are indicated with a solid line or a broken line, for example) may be used instead of the images having different colors.

The shape of the frame images F is not limited to the rectangular shape, and a shape in accordance with the shape displayed on the display unit 106 may be used.

Third Embodiment

Figure 10:
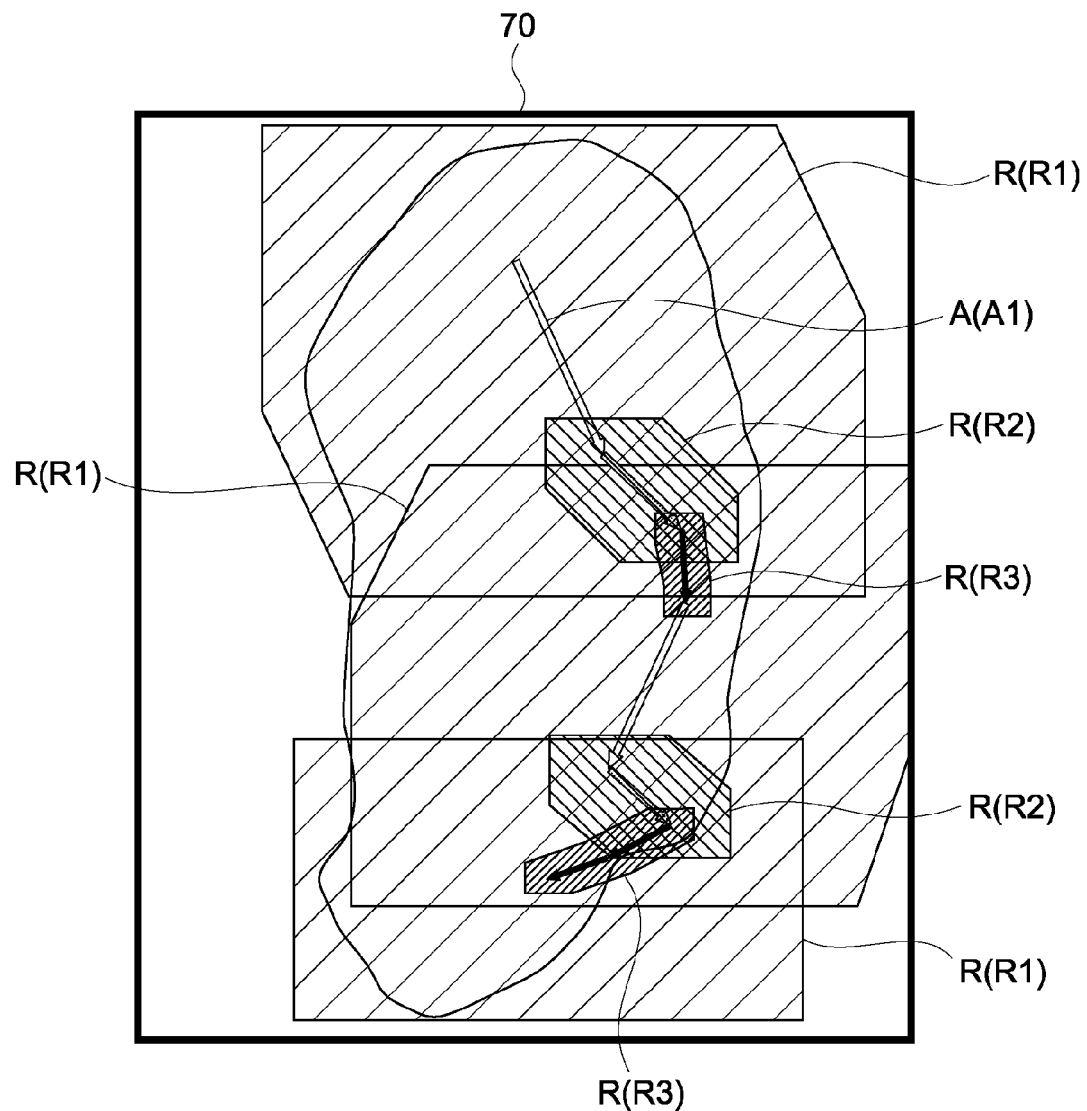
FIG. 10 is a diagram showing an entire image at an arbitrary resolution according to a second embodiment of the present disclosure.

FIG. 10 is a diagram showing an entire image at an arbitrary resolution according to another embodiment of the present disclosure.

In this embodiment, history images including outline images R (R1, R2, R3, . . . ) are composed in an entire image 70 at an arbitrary resolution. The outline images R indicate an entire outline in which display ranges of partial images for each observation magnification in the entire image are combined. Further, the arrow images A are also generated. The outline images R also function as the display-range emphasizing images. In addition, the colors of the outline images R differ depending on the observation magnifications. Therefore, the user can intuitively grasp the observation magnification.

As described above, the whole of the outline images R in which the display ranges are combined is generated, with the result that the user can reliably avoid the risk of missing the observation target object.

Fourth Embodiment

Figure 11:
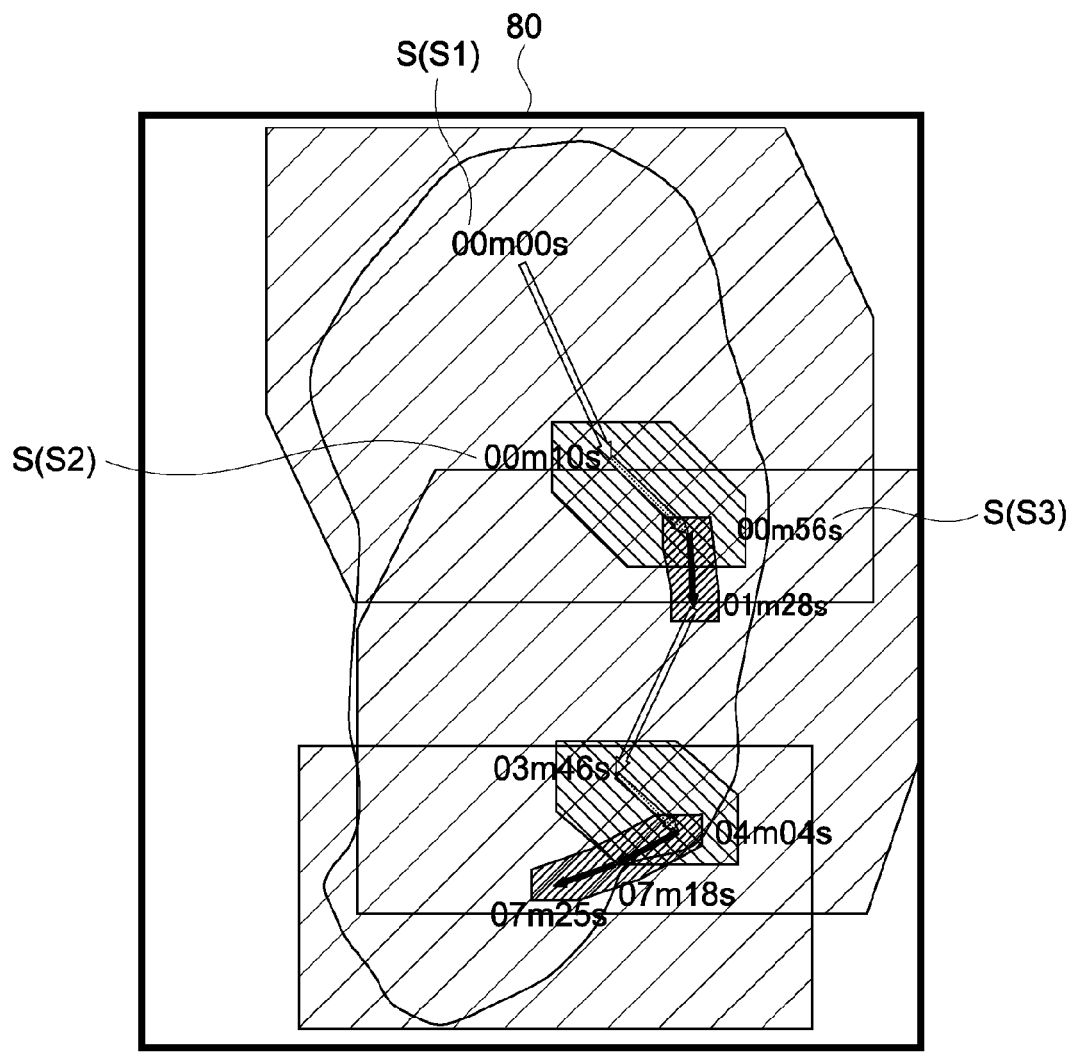
FIG. 11 is a diagram showing an entire image at an arbitrary resolution according to a third embodiment of the present disclosure.

FIG. 11 is a diagram showing an entire image at an arbitrary resolution according to another embodiment of the present disclosure.

An entire image 80 at an arbitrary resolution according to this embodiment is obtained by further composing time-stamp images S (S1, S2, S3, . . . ) in the entire image 70 at the arbitrary resolution shown in FIG. 10. The time-stamp images S function as the order emphasizing images. As a result, the user can easily grasp the time course of the traces of the display ranges. The time-stamp images S may be generated based on time information of the sampling out of the history information 20 shown in FIG. 7.

Fifth Embodiment

Figure 12:
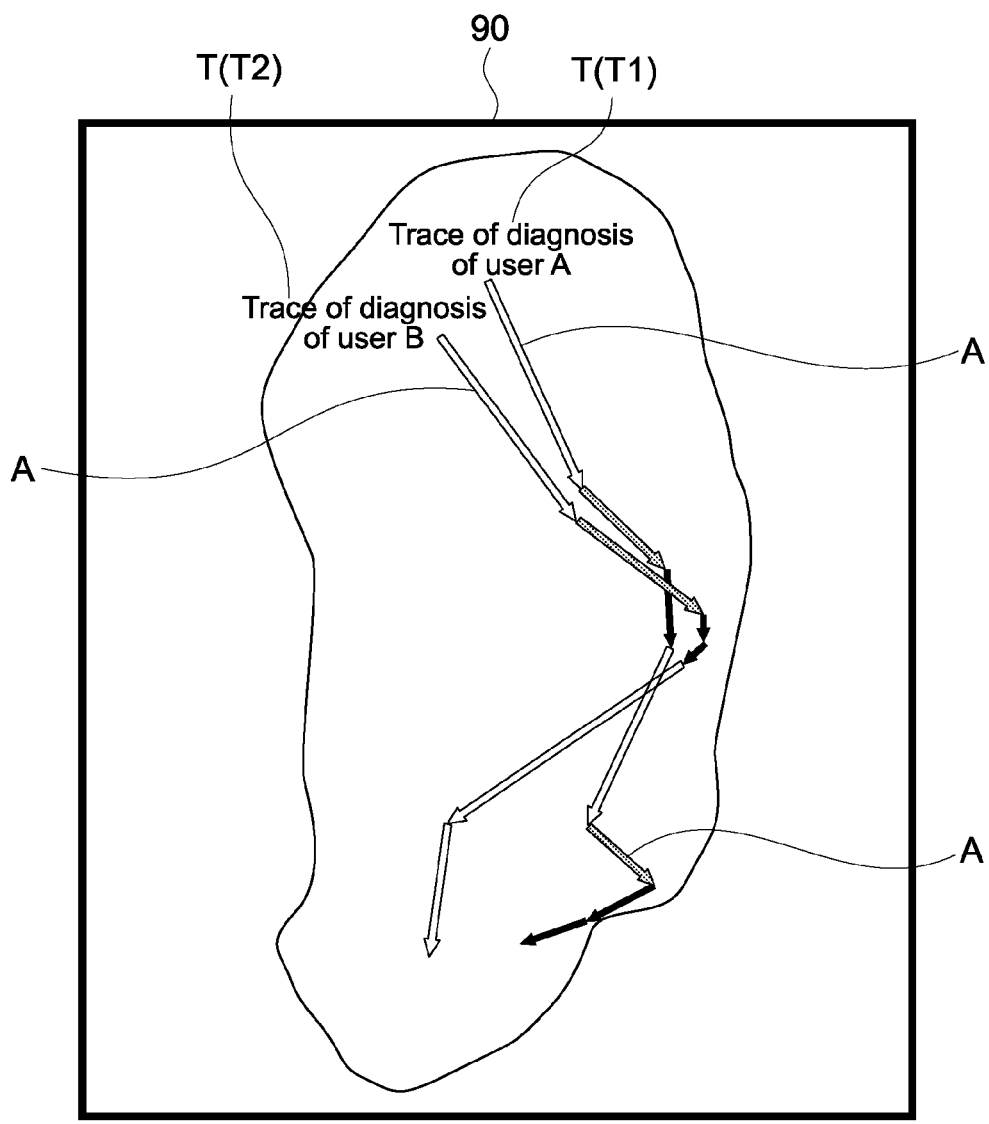
FIG. 12 is a diagram showing an entire image at an arbitrary resolution according to a fourth embodiment of the present disclosure.

FIG. 12 is a diagram showing an entire image at an arbitrary resolution according to another embodiment of the present disclosure.

In the entire image 90 at an arbitrary resolution according to this embodiment, user identification images T (T1 and T2) for identifying users are composed in the entire image at the arbitrary resolution. The user identification images T are text-formed images each including a name of a user, for example, "trace of diagnosis of user A" or "trace of diagnosis of user B".

The entire image 90 at the arbitrary resolution as described above is obtained by associating the history information items generated by the PC 100 through the observations for the users with the identification information items for identifying the users and storing the associated information items in the storage unit 108 or the like. That is, the history information 20 (see, FIG. 7) only has to be generated for each user. The text-formed images only has to be generated based on information on the user name of the PC 100 of each user or information on a name that is manually input after the termination of the observation of the images by the user.

The user identification images T are not limited to the text-formed images. The user identification images T may be particular mark images that are set for each user or arrow images that are set as images different depending on the users. The number of users may be three or more. The history images may be composed in different layers depending on the identification information items. In this case, the PC 100 or the like associates the identification information with the layer information to be stored in the storage unit 108 or the like.

Images in combination of at least two of the features in the entire images at the arbitrary resolutions according to the first to fifth embodiments described above may be generated in the entire image at the arbitrary resolution.

Another Embodiment

The present disclosure is not limited to the above embodiments, and other various embodiments are conceivable.

In the above, the mode is described in which the image data that forms the image pyramid structure 50 is stored in the storage unit 108 of the PC 100. However, instead of the PC 100, another computer or a server may store the image data that forms the image pyramid structure 50, and the PC 100 used by the user as a terminal apparatus may access the computer or the server to receive the image data. In this case, the PC 100 as the terminal apparatus and the server or the like may be connected via a network such as a LAN and a WAN. In particular, the use of the WAN can realize telepathology, telediagnosis, or the like.

In the above, the mode is described in which, as the original image of the image pyramid structure 50, one original image is generated with respect to the one observation target object 15. However, with respect to the one observation target object 15, a plurality of original images may be generated at different focus points in the thickness direction of the observation target object 15 which is a focus direction of the optical microscope. This is called Z-stack, which is a function to deal with the case where tissues or cells may have different shapes also in the thickness direction of the observation target object 15. The scanner apparatus has the Z-stack function in many cases, and about 5 to 10 or 10 to 30 original images are generated.

In addition, the scanner apparatus, the PC 100, or another computer generates, from the plurality of original images thus generated, entire images at resolutions for each original image (with respect to the plurality of original images) by a known compression method or a known compression method at a time when a thumbnail image is generated, for example. That is, the entire images at a plurality of focus points are generated with respect to the entire image at least one resolution. Specifically, in this case, the total count of the entire images of the image pyramid structure shown in FIG. 2 is determined to be M*L in which M represents an existence count of the resolutions and L represents an existence count of the focus points. L falls within the range of, for example, 5 to 30 as described above, but is not limited to this range. Hereinafter, one of the plurality of images that are generated at different focus points in the focus direction of the observation target and that each include the plurality of original images will be referred to as a different-focus-point entire image.

In the case where such a different-focus-point entire image is generated, the PC 100 or another computer performs the following processing, for example. That is, the PC 100 or the like only has to associate positional information of different partial images as a part of the image in the different-focus-point entire image with focus information of those different partial images, and further store the association information as part of the history information 20. As a result, for example, the PC 100 can generate a focus-point emphasizing image that indicates the focus information in the entire image 40, 60, 70, 80, or 90 at the arbitrary resolution. Consequently, the user can also grasp the history on the focus points. The focus-point emphasizing image is represented by at least one of a character, a sign, and a figure.

In the above description, the sampling period is set to be constant. The sampling period in the case where the storing process is performed on the history information of the partial image may be changed when necessary by the user. Alternatively, the sampling period may be controlled variably depending on the observation magnifications (resolutions). For example, the CPU 101 of the PC 100 sets the sampling period to a first time period in the case of the observation at a first resolution, and sets the sampling period to a second time period that is shorter than the first time period in the case where a second resolution that is higher than the first resolution is set through a user operation. As a result, the number of partial images at a higher magnification can be greater than the number of partial images at a lower magnification.

Conversely, the CPU 101 of the PC 100 may set the sampling period to the first time period in the case of the observation at the first resolution, and may set the sampling period to the second time period that is longer than the first time period in the case where the second resolution that is higher than the first resolution is set through the user operation.

The above-mentioned processing can allow the user to select importance or priority with respect to the partial image of the high magnification and the partial image of the low magnification.

Alternatively, the CPU 101 of the PC 100 counts a display time period that is a time period during which one partial image is displayed, and compares the display time period with a certain sampling period. In the case where the display time period is longer than the sampling period, the CPU 101 may store the display time period as the history information of the one partial image. As a result, in the case where the display time period is shorter than the sampling period, the CPU 101 can omit processing of storing the history information of the partial image whose display time period is short. Thus, the processing performed by the CPU 101 becomes more efficient, resulting in reduction in quantity of memory thereof.

In the above embodiments, the image pyramid structure 50 is formed of the image group constituted of the entire images at the resolutions that are generated and stored in advance. However, the PC 100, another computer, or the like may generate, when necessary, an entire image that is not generated and stored in advance. For example, the PC 100 or the like can generate an entire image at a resolution corresponding to the observation magnification of 30 times by interpolation from the entire images whose observation magnifications of 20 times and 40 times which are generated and stored in advance.

The PC is used as the information processing apparatus according to the above embodiments, but a dedicated information processing apparatus may be used instead of the PC. Further, the information processing apparatus is not limited to an apparatus that implements the above-described information processing in cooperation with the hardware resource and the software. Dedicated hardware may implement the above-described information processing.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The invention claimed is:

1. A method of controlling display of a pathological microscopic image, the method comprising:
controlling a display device to display a first area and a second area of a pathological microscopic image, wherein the first area of the pathological microscopic image is configured to be displayed in a first resolution and the second area of the pathological microscopic image is configured to be displayed in a second resolution; and
controlling the display device to display a first part of the first area in a first color different from an intrinsic color of the pathological microscopic image, wherein the first part of the first area corresponds to the second area of the pathological microscopic image, and wherein the first color includes one or more colors,
wherein the first color is representative of history information associated with an observation of the pathological microscopic image.

2. The method of claim 1, wherein the first color is representative of a magnification level of the second area of the pathological microscopic image.

3. The method of claim 1, wherein the history information includes positional information and observation magnification information.

4. The method of claim 1, wherein the history information includes positional information and observation area information.

5. The method of claim 1, wherein the history information includes positional information and observation time information.

6. The method of claim 1, wherein the history information includes positional information and observation order information.

7. The method of claim 6, wherein the observation order information includes an arrow image.

8. The method of claim 1, wherein the history information includes positional information and observation person information.

9. The method of claim 1, wherein the history information includes positional information and observation focus information.

10. The method of claim 1, further comprising a sampling period, wherein the sampling period is constant.

11. The method of claim 1, further comprising a sampling period, wherein the sampling period is variably depending on observation magnification of the pathological microscopic image.

12. The method of claim 1, wherein the pathological microscopic image includes at least a part of biological tissue.

13. The method of claim 1, wherein the first color is variable depending on a magnification level of the second area of the pathological microscopic image.

14. The method of claim 1, wherein the first color increases intensity as a magnification level of the second area of the pathological microscopic image increases.

15. The method of claim 1, wherein the pathological microscopic image has a pyramid structure.

16. The method of claim 1, wherein the first resolution is fixed, and wherein the second resolution is variable.

17. The method of claim 1, wherein the first part of the first area is displayed in the first color after the second area of the pathological microscopic image is displayed in a predetermined period of time.

18. The method of claim 1, wherein the first part of the first area is displayed in the intrinsic color of the pathological microscopic image until the second area of the pathological microscopic image is displayed in the predetermined period of time.

19. The method of claim 1, wherein the first area and the second area of the pathological microscopic image are displayed in proximity thereof in the display device.

20. An apparatus for controlling display of a pathological microscopic image, the apparatus comprising:
a processor; and
a memory device operatively coupled to the processor, the memory device storing instructions that cause the processor to:
control a display device to display a first area and a second area of a pathological microscopic image, wherein the first area of the pathological microscopic image is configured to be displayed in a first resolution and the second area of the pathological microscopic image is configured to be displayed in a second resolution; and
control the display device to display a first part of the first area in a first color different from an intrinsic color of the pathological microscopic image, wherein the first part of the first area corresponds to the second area of the pathological microscopic image, and wherein the first color includes one or more colors,
wherein the first color is representative of history information associated with an observation of the pathological microscopic image.

21. The apparatus of claim 20, wherein the first color is representative of a magnification level of the second area of the pathological microscopic image.

22. The apparatus of claim 20, wherein the history information includes positional information and observation magnification information.

23. The apparatus of claim 20, wherein the history information includes positional information and observation area information.

24. The apparatus of claim 20, wherein the history information includes positional information and observation time information.

25. The apparatus of claim 20, wherein the history information includes positional information and observation order information.

26. The apparatus of claim 25, wherein the observation order information includes an arrow image.

27. The apparatus of claim 20, wherein the history information includes positional information and observation person information.

28. The apparatus of claim 20, wherein the history information includes positional information and observation focus information.

29. The apparatus of claim 20, wherein the apparatus sets a sampling period, wherein the sampling period is constant.

30. The apparatus of claim 20, wherein the apparatus sets a sampling period, wherein the sampling period variably depends on observation magnification of the pathological microscopic image.

31. The apparatus of claim 20, wherein the pathological microscopic image includes at least a part of biological tissue.

32. The apparatus of claim 20, wherein the first color is variable depending on a magnification level of the second area of the pathological microscopic image.

33. The apparatus of claim 20, wherein the first color increases intensity as a magnification level of the second area of the pathological microscopic image increases.

34. The apparatus of claim 20, wherein the pathological microscopic image has a pyramid structure.

35. The apparatus of claim 20, wherein the first resolution is fixed, and wherein the second resolution is variable.

36. The apparatus of claim 20, wherein the first part of the first area is displayed in the first color after the second area of the pathological microscopic image is displayed in a predetermined period of time.

37. The apparatus of claim 36, wherein the first part of the first area is displayed in the intrinsic color of the pathological microscopic image until the second area of the pathological microscopic image is displayed in the predetermined period of time.

38. The apparatus of claim 20, wherein the first area and the second area of the pathological microscopic image are displayed in proximity thereof in the display device.

39. A non-transitory computer-readable medium storing instructions structured to cause an information processing apparatus to:
control a display device to display a first area and a second area of a pathological microscopic image, wherein the first area of the pathological microscopic image is configured to be displayed in a first resolution and the second area of the pathological microscopic image is configured to be displayed in a second resolution; and
control the display device to display a first part of the first area in a first color different from an intrinsic color of the pathological microscopic image, wherein the first part of the first area corresponds to the second area of the pathological microscopic image, and wherein the first color includes one or more colors,
wherein the first color is representative of history information associated with an observation of the pathological microscopic image.

40. The non-transitory computer-readable medium of claim 39, wherein the first color is variable depending on a magnification level of the second area of the pathological microscopic image.

41. The non-transitory computer-readable medium of claim 39, wherein the first color increases intensity as a magnification level of the second area of the pathological microscopic image increases.

42. The non-transitory computer-readable medium of claim 39, wherein the first part of the first area is displayed in the first color after the second area of the pathological microscopic image is displayed in a predetermined period of time.

43. The non-transitory computer-readable medium of claim 42, wherein the first part of the first area is displayed in the intrinsic color of the pathological microscopic image until the second area of the pathological microscopic image is displayed in the predetermined period of time.

44. A system for controlling display of a pathological microscopic image, the apparatus comprising:
a display device;
a processor;
a memory device operatively coupled to the processor, the memory device storing instructions that cause the processor to:
display on the display device a first area and a second area of a pathological microscopic image, wherein the first area of the pathological microscopic image is configured to be displayed in a first resolution and the second area of the pathological microscopic image is configured to be displayed in a second resolution; and
display on the display device a first part of the first area in a first color different from an intrinsic color of the pathological microscopic image, wherein the first part of the first area corresponds to the second area of the pathological microscopic image, and wherein the first color includes one or more colors,
wherein the first color is representative of history information associated with an observation of the pathological microscopic image.

45. The system of claim 44, wherein the first color is variable depending on a magnification level of the second area of the pathological microscopic image.

46. The system of claim 44, wherein the first color increases intensity as a magnification level of the second area of the pathological microscopic image increases.

47. The system of claim 44, wherein the first part of the first area is displayed in the first color after the second area of the pathological microscopic image is displayed in a predetermined period of time.

48. The system of claim 47, wherein the first part of the first area is displayed in the intrinsic color of the pathological microscopic image until the second area of the pathological microscopic image is displayed in the predetermined period of time.

* * * * *